United States Patent [19]

Nowicki et al.

[11] Patent Number: 4,892,970

[45] Date of Patent: Jan. 9, 1990

[54] STAGED AROMATICS OXIDATION IN AQUEOUS SYSTEMS

[75] Inventors: Neal R. Nowicki, Naperville; James D. Lowry, Jr., Bolingbrook, both of Ill.

[73] Assignee: Amoco Corporation, Chicago, Ill.

[21] Appl. No.: 814,510

[22] Filed: Dec. 30, 1985

[51] Int. Cl.⁴ .................... C07C 51/265; C07C 57/34
[52] U.S. Cl. ...................... 22/413; 562/480; 562/421
[58] Field of Search .............. 562/413, 421, 480

[56] References Cited

U.S. PATENT DOCUMENTS 3,406,196 10/1968 Lewis et al. .................. 562/413
3,595,908 7/1971 Lumbrosor et al. ........... 562/413

FOREIGN PATENT DOCUMENTS 13255 1/1980 Japan ............................ 562/421

Primary Examiner—Vivian Garner
Attorney, Agent, or Firm—James R. Henes; William H. Magidson; Ralph C. Medhurst

[57] ABSTRACT

Improved acid yield and product quality are realized in the oxidation of aromatic hydrocarbons in a two-stage process, employing an aqueous solvent system and an increased proportion of bromine, and, optionally, of catalytic metals, in the second stage.

22 Claims, No Drawings

STAGED AROMATICS OXIDATION IN AQUEOUS SYSTEMS

BACKGROUND OF THE INVENTION

This invention relates to an improved oxidation process for the conversion of one or more aromatic hydrocarbon materials, having oxidizable substituents, to their corresponding acid derivative. More particularly, the process of this invention relates to a staged oxidation in an aqueous medium.

It is well known that aromatic hydrocarbons, having at least one, and preferably two or more, oxidizable substituent group may be converted into carboxylic acid products by effecting oxidation of such groups under controlled conditions. Such conditions have generally included the use of a known oxidation catalyst together with a suitable solvent such as a low molecular weight aliphatic carboxylic acid, such as acetic acid. A typical catalyst system comprises compounds of manganese and/or cobalt, together with a bromine-affording material. U.S. Pat. No. 3,092,658 describes the use of such a process for the continuous oxidation of substituted aromatic hydrocarbons to their corresponding carboxylic acid derivatives, particularly for the preparation of the isomeric phthalic acids from their xylene precursors in an acetic acid solvent.

In such an oxidation system a significant loss of acetic acid occurs, attributable to oxidation, handling losses, volatility, and the like. In order to avoid this economic penalty, attempts have been made to operate without a solvent but without significant success. A more promising approach has involved the use of a solvent system comprising water.

U.S. Pat. Nos. 4,258,209 and 4,278,810, commonly assigned, employ at least 5 wt % water, together with toluic, benzoic and/or acetic acid, as solvent, to provide an essentially homogeneous reaction mixture. More metal oxidation catalyst is required as the proportion of water increases. Processing may be batch or continuous but no bromine is employed. Acid yields are low, oxidation is incomplete, and purification of the acid product requires expensive processing.

U.S. Pat. No. 4,323,699 (and related European Patent Application 81302189.6) employs an aqueous medium and an iodine promoter. A heavy metal-bromine catalyst is present in a batch system and, again, yields of acid product are low while large quantities of intermediate oxidation products and by-products are obtained.

Earlier prior art examples include U.S. Pat. No. 3,012,038, wherein water is treated as the equivalent of lower aliphatic acids, aromatic hydrocarbons, halogen derivatives of benzene, and aromatic acids, as a suitable solvent under conditions selected to minimize corrosion of oxidation equipment. In another example, U.S. Pat. No. 3,711,539 permits water (an oxidation product) to vaporize from the reaction system to limit its concentration. Multi-state oxidation systems are disclosed in commonly assigned U.S. Pat. No. 3,064,044 and Canadian patent no. 704,424, each employing the conventional aliphatic acid solvent.

Further attention has been given to the use of an aqueous solvent system in such aromatic oxidations in an attempt to maximize the effectiveness of raw material oxidation, to lower the impurity level significantly to improve quality of product, and to provide an improved oxidation process from an economic viewpoint.

Summary of the Invention

The process of this invention relates to an improved continuous staged process for the oxidation of aromatic hydrocarbons and derivatives, having oxidizable substituents, in an aqueous solvent system. Oxidation is generally effected at elevated temperatures in two stages, employing ionic catalytic metals, including manganese, and bromine. Oxidation is substantially completed in the second stage at a higher reaction temperature and in the presence of a higher proportion of bromine and, optionally, of manganese.

It is an object of this invention to provide an improved and commercially competitive oxidation process for the conversion of aromatic hydrocarbon materials to corresponding aromatic carboxylic acids.

It is another object of this invention to provide an improved and economic process for the oxidation of paradisubstituted benzene hydrocarbons to the corresponding dibasic carboxylic acid, i.e., terephthalic acid, in condition for ready purification for use in various commercial processes.

DESCRIPTION OF THE INVENTION

The process of this invention relates to the oxidation of substituted aromatic hydrocarbon materials, having oxidizable substituents, to corresponding aromatic carboxylic acids in an aqueous solvent system. The improved process of this invention utilizes the surprising finding that, in a staged oxidation process, higher acid yields and better product quality are achieved by effecting substantially complete oxidation in a second stage in the presence of an increased proportion of a bromine-affording substance and, optionally, of an ionic catalytic metal, such as manganese, as well.

Feedstock components for the process of this invention include aromatic hydrocarbons having at least one oxidizable substituent group capable of being oxidized to a corresponding carboxylic acid or the derivative product. Preferred feedstock components include disubstituted benzene materials having any of a variety of substituents selected from the class consisting of alkyl, hydroxyalkyl, aldehyde, and carboalkyl groups, together with mixtures of these. Particularly preferred feedstock components include the para-disubstituted benzene derivatives having alkyl groups as substituents. The alkyl groups preferably contain 1-4 carbon atoms, most preferably methyl groups. Accordingly, an especially preferred feedstock component is para-xylene.

Feedstock components also include catalyst materials such as ionic catalytic metals, including manganese and at least one additional metal selected from the class consisting of cobalt, nickel, zirconium, and mixtures thereof. In a preferred feed mixture the ionic catalytic metals are cobalt and manganese. A further catalyst component of the feed mixture is a bromine-affording material, which may be elemental bromine, a bromide or bromate salt, hydrobromic acid, a bromine-substituted organic compound, or a mixture of any or all of these.

In the process of this invention, a typical feed mixture comprises, per 100 weight parts of aromatic hydrocarbon materials, from about 5 to about 100, preferably from about 20 to about 80, most preferably from about 30 to about 60, weight parts of water. The feed also contains from about 0.1 to about 5.0, preferably from about 0.2 to about 4.0, most preferably from 0.4 to about 3.0, weight parts of ionic catalytic metals. Additionally, the components in the feed mixture include from about 10 to about 300, preferably from about 10 to about 100, most preferably from 10 to about 50, atoms percent of bromine, based on total catalytic metals.

In the feed mixture of this invention, the preferred catalytic metals are manganese and cobalt, present in an atom ratio of manganese to cobalt within the range from about 0.5 to about 3.0.

In the process of this invention, the feed mixture, as set forth above, is introduced to a first oxidation stage, together with a stoichiometric excess of an oxygen-containing gas, such as air, oxygen, or a mixture thereof, said oxidation stage being maintained at a temperature within the range from about 300° to about 410° F. and at a pressure sufficiently high to maintain the oxidation reaction mixture substantially in the liquid phase. The first oxidation step is preferably conducted at a temperature within the range from about 330° to about 370°, most preferably from about 330° to about 350° F.

In the conduct of the oxidation process of this invention, the oxidation conversion of the feed aromatic material is generally carried to from about 60 to about 95%, preferably from about 70 to about 85%, most preferably from about 75 to about 85%, completion in the first oxidation stage. In this manner, conversion to by-products is minimized. Although much of the oxidation has produced only oxidation intermediates at this point because of low severity, the oxidation can be readily completed in a second oxidation stage.

The effluent phase, recovered from the first oxidation stage, is sent to second oxidation stage after the addition of supplemental bromine-affording material to provide from about 50 to about 500, preferably from about 100 to about 300, most preferably from about 200 to about 300, atom percent bromine, based on total catalytic metals in the effluent phase. Supplemental manganese can also be added to provide an atom ratio of manganese to cobalt within the range from about 3.0 to about 6.0. The effluent phase may also be supplemented with water as needed to provide a workable, or pumpable, slurry phase, comprising a mixture of acid product, oxidation intermediates, water, and catalytic agents.

The slurry phase is then processed further in the second oxidation stage of this invention, in admixture with additional oxygen-containing gas, at a higher temperature within the range from about 400° to about 480° F., preferably from about 400° to about 450° F., most preferably from about 430° to about 450° F., and at a pressure sufficiently high to maintain the slurry substantially in the liquid phase. The conditions maintained in the second oxidation stage provide substantially complete oxidation of any remaining feed aromatics together with the various intermediate oxidation products. It has been found that the added bromine, present in the second oxidation stage, effectively suppresses decarboxylation reactions that typically occur at higher oxidation temperatures. Without this added bromine, consistent achievement of acceptable product yields and product quality would not be possible.

The following examples are illustrative, without limitation, of the improved oxidation process of this invention.

EXAMPLE 1

Para-xylene was oxidized to terephthalic acid under the conditions shown in Table I in a stirred reactor. The ratio of manganese to cobalt was maintained substantially constant from stage to stage but the ratio of bromine to total metals was increased eight-fold. The slurry from the second stage was separated and analyzed for product, high molecular weight components (HMWC), and key color indicators, including dicarboxyfluorenone (DCF) and dicarboxyanthraquinone (DCAq), as well as a general quantification of fluorescent compounds, characterized here as the relative fluorescence concentration (RFCuv). Product quality was characterized in terms of solid impurities, expressed as parts per million (ppm). Results are presented in Table I.

EXAMPLE 2

The procedure of Example 1 was essentially repeated except that the ratio of bromine to total metals was maintained constant in the two oxidation stages. Results are presented in Table I.

By reference to Table I, it is seen that increasing the bromine concentration in the second oxidation stage led to a much lower level of undesirable impurities as well as a lower level of incompletely oxidized intermediates (toluic acid and 4-carboxybenzaldehyde).

EXAMPLE 3

The procedure of Example I was essentially repeated under the conditions shown in Table II, except that the total metals and ratio of manganese to cobalt were increased in the second stage as well as the proportion of bromine.

EXAMPLE 4

Para-xylene was oxidized, in a stirred reactor, employing acetic acid as solvent with catalytic metals and bromine present in proportions typical of commercial operations as shown in Table II. Product was worked up in the same manner as second-stage product from the aqueous systems.

By reference to Table II it is seen that the total metals requirement for the water-based oxidation is some 35 times greater than that required for the acetic acid system. The water-based oxidation provided a much lower concentration of intermediates and fluorescent by-products. The water-based oxidation also produced appreciable levels of bromoterephthalic acid (Br-TA). It was further noted that 0.07 pound of acetic acid, per pound of terephthalic acid product, was lost by reactor burning in Example 4.

TABLE I

| Oxidation of Para-Xylene: Water Solvent | | | | |
|---|---|---|---|---|
| Example | 1 | | 2 | |
| Oxidation Stage | 1 | 2 | 1 | 2 |
| Process Conditions | | | | |
| Conversion, moles $O_2$/PX | 2.74 | 0.47 | 2.58 | 0.47 |
| Temperature, °F. | 380 | 453 | 360 | 444 |
| Time, min. | 75 | 60 | 75 | 60 |
| Pressure, $O_2$, psi | 8 | 11 | 12 | 10 |
| Total Pressure, psig | 525 | 510 | 525 | 515 |
| Stirring Rate, rpm | 1750 | 1350 | 1900 | 1350 |
| Co + Mn, wt. % PX | 2.7 | 3.3 | 2.3 | 3.9 |
| Mn/Co | 3.0 | 3.0 | 3.0 | 3.0 |
| Br/Co + Mn | 0.35 | 2.8 | 1.8 | 1.8 |
| Solvent Ratio, $H_2O$/PX | 0.3 | 2.3 | 0.3 | 2.3 |
| Product Distribution (wt. % slurry) | | | | |
| PX | — | — | — | — |
| Tolualdehyde | — | — | — | — |
| Toluic acid | — | 0.08 | — | 0.17 |
| 4-CBA | — | 0.18 | — | 0.48 |
| Terephthalic acid | — | 33.0 | — | 33.5 |
| HMWC | — | 0.20 | — | 0.56 |

TABLE I-continued

Oxidation of Para-Xylene: Water Solvent

| Example | 1 | | 2 | |
|---|---|---|---|---|
| Oxidation Stage | 1 | 2 | 1 | 2 |
| Br—TA | — | 0.53 | — | 0.31 |
| Others | — | 0.48 | — | 0.49 |
| $CO_2$ (% PX) | 1.07 | 0.10 | 1.23 | 1.11 |
| Product Quality (ppm) | | | | |
| 4-CBA | | 0.53 | | 1.35 |
| Toluic acid | | 0.23 | | 0.48 |
| DCF | | 440 | | 610 |
| DC Aq | | 56 | | 158 |
| RFC (uv) | | 100 | | 1100 |

TABLE II

Oxidation of Para-Xylene: Solvent Comparison

| Example | 3 | | 4 |
|---|---|---|---|
| Oxidation Stage | 1 | 2 | 1 |
| Solvent | $H_2O$ | $H_2O$ | HOAc |
| Process Conditions | | | |
| Conversion, moles $O_2$/PX | 2.41 | 0.68 | 3.21 |
| Temperature, °F. | 366 | 429 | 439 |
| Time, min. | 80 | 60 | 60 |
| Pressure, $O_2$, psi | 14 | 12 | 6 |
| Total Pressure, psig | 450 | 440 | 4.5 |
| Stirring Rate, rpm | 2100 | 1350 | 1250 |
| Co + Mn, wt. % PX | 0.82 | 3.5 | 0.094 |
| Mn/Co | 0.53 | 2.9 | 3.2 |
| Br/Co + Mn | 0.80 | 2.5 | 0.69 |
| Solvent Ratio, $H_2O$/PX | 0.3 | 2.3 | 2.8 |
| Product Distribution (wt. % slurry) | | | |
| PX | | — | — |
| Tolualdehyde | | — | — |
| Toluic acid | | 0.16 | 0.43 |
| 4-CBA | | 0.35 | 1.50 |
| Terephthalic acid | | 33.66 | 33.02 |
| HMWC | | 0.17 | 0.08 |
| Br—TA | | 0.84 | — |
| Others | | 0.22 | 0.37 |
| $CO_2$ (% PX) | | 3.06 | 1.75 |
| Acetic Acid Loss (lb/lb TA) | | — | 0.07 |
| Product Quality (ppm) | | | |
| 4-CBA | | 0.99 | 1.21 |
| Toluic acid | | 0.45 | 4.24 |
| DCF | | 430 | 83 |
| DC Aq | | 75 | 22 |
| RFC (uv) | | 120 | 480 |

We claim:

1. A continuous, staged process for the oxidation of benzenes disubstituted with oxidizable substituents selected from the class consisting of alkyl, hydroxyalkyl, aldehyde, carboalkyl groups and mixtures thereof, to their corresponding acid derivatives in an aqueous solvent system, comprising the steps of:

(a) affording a feed mixture comprising 100 weight parts of the aforesaid disubstituted benzenes, from about 5 to about 100 weight parts of water, from about 0.1 to about 5.0 weight parts of ionic catalytic metals, comprising manganese and at least one other catalytic metal selected from the class consisting of cobalt, nickel, zirconium and mixtures thereof, and bromine in an amount within the range from about 10 to about 300 atom percent, based on total catalytic metals;

(b) partially oxidizing said feed mixture in a first oxidation stage, in the presence of an oxygen-containing gas, at a temperature within the range from about 300° to about 410° F. and at a pressure sufficiently high to maintain the mixture substantially in the liquid phase;

(c) recovering from said first oxidation stage an effluent phase, wherein the degree of conversion to acid derivatives is within the range from about 60% to about 95%.

(d) adding to said effluent phase supplemental bromine to raise the concentration therein of total bromine to a concentration that is higher than the bromine concentration in the first oxidation stage and that is in the range of from about 50 to about 500 atom percent, based on total catalytic metals, and supplemental water in an amount to provide a workable slurry phase;

(e) substantially completely oxidizing the resulting slurry phase in a second oxidation stage, in the presence of an oxygen-containing gas, at a temperature within the range from about 400° to about 480° F. and at a pressure sufficiently high to maintain the slurry substantially in the liquid phase; and (f) recovering from said second oxidation stage an acid derivative product.

2. The process of claim 1 wherein the disubstituted benzenes consist of para-disubstituted benzenes and the corresponding acid derivative product is terephthalic acid.

3. The process of claim 2 wherein the substituents in the para-disubstituted benzenes are alkyl groups having from one to four carbon atoms.

4. The process of claim 3 wherein the alkyl groups are methyl groups.

5. The process of claim 2 wherein the degree of conversion to terephthalic acid in the first oxidation stage is within the range from about 70 to about 85%.

6. The process of claim 5 wherein the degree of conversion to terephthalic acid in the first oxidation stage is within the range from about 75 to about 85%.

7. The process of claim 1 wherein the catalytic metals in the feed mixture are cobalt and manganese.

8. The process of claim 6 wherein the atom ratio of manganese to cobalt in the feed mixture is within the range, from about 0.5 to about 3.0.

9. The process of claim 8 wherein supplemental manganese is added to the resulting slurry phase to provide, in the second oxidation stage, an atom ratio of manganese to cobalt within the range from about 3.0 to about 6.0.

10. The process of claim 1 wherein the feed mixture comprises from about 20 to about 80 weight parts of water, based on aromatic hydrocarbon materials.

11. The process of claim 10 wherein the feed mixture comprises from about 30 to about 60 weight parts of water.

12. The process of claim 1 wherein the feed mixture comprises from about 0.2 to about 4.0 weight parts of ionic catalytic metals.

13. The process of claim 12 wherein the feed mixture comprises from about 0.4 to about 3.0 weight parts of ionic catalytic metals.

14. The process of claim 1 wherein the feed mixture comprises from about 10 to about 100 atom percent bromine, based on total catalytic metals.

15. The process of claim 14 wherein the feed mixture comprises from about 10 to about 50 atom percent bromine, based on total catalytic metals.

16. The process of claim 1 wherein the temperature in the first oxidation stage is maintained within the range from about 330 to about 370° F.

17. The process of claim 16 wherein the temperature in the first oxidation stage is maintained within the range from about 330 to about 350° F.

18. The process of claim 1 wherein supplemental bromine is added to the effluent phase to provide total bromine in an amount within the range from about 100 to about 300 atoms percent, based on total catalytic metals.

19. The process of claim 18 wherein supplemental bromine is added to the effluent phase to provide total bromine in an amount within the range from about 200 to about 300 atom percent, based on total catalytic metals.

20. The process of claim 1 wherein the resulting slurry phase is oxidized in a second oxidation stage maintained at a temperature within the range from about 400 to about 450° F.

21. The process of claim 20 wherein the resulting slurry phase is oxidized in a second oxidation stage maintained at a temperature within the range from about 400 to about 450° F.

22. A continuous, staged process for the oxidation of para-xylene to terephthalic acid in an aqueous solvent system, comprising the steps of:
   (a) preparing a feed mixture comprising 100 weight parts of para-xylene, about 30 weight parts of water, a total of about 3 weight parts of ionic cobalt and manganese wherein the atom ratio of manganese to cobalt is about 3.0, and sufficient bromine to provide an atom ratio of bromine to total metals of about 0.35;
   (b) oxidizing said feed mixture in a first oxidation stage, in the presence of oxygen-containing gas, maintained at a temperature of about 340° F. and at a pressure sufficiently high to maintain the mixture substantially in the liquid phase, to effect about 80% conversion of para-xylene to terephthalic acid;
   (c) recovering an effluent phase from the first oxidation stage;
   (d) adding to the effluent phase from the first oxidation stage supplemental bromine to raise the concentration therein of bromine to an atom ratio of bromine to total metals that is about 2.8 and that is higher than the atom ratio of bromine to total metals in the first oxidation stage, and with supplemental water in an amount to provide a workable slurry phase;
   (e) substantially completing the oxidation of the resulting slurry phase in a second oxidation stage, in the presence of an oxygen-containing gas, maintained at a temperature of about 450° F. and a pressure sufficiently high to maintain the slurry substantially in the liquid phase; and
   (f) recovering from said second oxidation stage a terephthalic acid product.

* * * * *